United States Patent [19]

Ogilvie

[11] Patent Number: 4,461,757

[45] Date of Patent: Jul. 24, 1984

[54] DIMETHYLAMINOMETHYLENATED ANTI-HERPES COMPOUNDS

[75] Inventor: Kelvin K. Ogilvie, Candiac, Canada

[73] Assignee: ens Bio Logicals Inc., Toronto, Canada

[21] Appl. No.: 468,877

[22] Filed: Feb. 23, 1983

[51] Int. Cl.³ .................. A61K 31/52; C07D 473/18
[52] U.S. Cl. ................................. 424/085; 424/200; 424/253; 544/276; 544/277
[58] Field of Search ............... 544/277, 276; 424/200, 424/253, 85

[56] References Cited

U.S. PATENT DOCUMENTS

| | | | |
|---|---|---|---|
| 4,323,573 | 4/1982 | Schaeffer | 544/276 |
| 4,347,360 | 8/1982 | Ogilvie | 544/276 |
| 4,355,032 | 10/1982 | Verheyden et al. | 544/276 |

Primary Examiner—Nicholas S. Rizzo
Attorney, Agent, or Firm—Murray, Whisenhunt & Ferguson

[57] ABSTRACT

2-(N,N-dialkylaminomethylene)-9-[[2-hydroxy-1-(hydroxymethyl)-ethoxy]methyl]guanine either alone or in admixture with interferon is active in treatment of herpes simplex type 1 viral infections.

10 Claims, No Drawings

DIMETHYLAMINOMETHYLENATED ANTI-HERPES COMPOUNDS

FIELD OF THE INVENTION

This invention relates to novel compounds and compositions having pharmaceutical activity, and more particularly to a novel guanine derivative compound, and compositions thereof, which are active against herpes virus infections.

BACKGROUND OF THE INVENTION AND PRIOR ART

Herpes simplex virus (HSV) infections are widespread in human populations, and pose a particularly difficult health problem. There is currently no cure for herpes infections. Many of the drugs currently in clinical use may not be effective in reducing the severity or duration of the systems. Even after the symptoms disappear, herpes virus tends to remain dormant in nerve tissue, only to be reactivated at a later date to an active phase of infection, causing lesions ("cold sores") and other symptoms to recur. A drug can be considered effective if it diminishes the severity of the lesions, allows for more rapid healing, extends the period between recurrences of herpes infections or stops recurrences altogther.

Herpes simplex virus is one member of the family "Herpetoviridae"; other members of this family which infect humans are varicella-zoster, cytomegalovirus and Epstein-Barr virus. The family also includes various members which attack animals. For example, there are three types of equine herpesvirus, a swine herpesvirus, a canine herpesvirus and a feline herpesvirus, among others.

As with all viruses, herpes virus invades healthy host cells on which it relies to provide its needs for replication. Herpes viruses code for some of the enzymes they need for replication, instead of relying completely on the host cell for all their needs. Hence, herpes viruses are subject to selective inhibition by certain drugs that interfere specifically with viral enzymes. A variety of drugs have been proposed and tested for treatment of HSV infections. For example, U.S. Pat. No. 4,199,574 Schaeffer, issued Apr. 22, 1980 discloses a wide variety of compounds said to be useful in such treatments, extensive testing of one of which (acycloguanosine or acyclovir, 9-[2-hydroxyethoxymethyl]guanine) has been reported in the literature, with sometimes promising results. Another drug which has been explored is 5-iododeoxyuridine (IDU), but this has been reported to be effective only against herpes infections of the eyes. It also has undesirable side effects, associated with toxicity to normal cells. Adenine arabinoside (ara-A), phosphonoformic acid (PFA), phosphonoacetic acid (PAA), 2-deoxy-D-glucose (2DG), and 5-(2-halogenovinyl)-2'-deoxyuridines as exemplified by bromovinyl-deoxyuridine (BVDU) and its iodo-analog are other drugs which have some demonstrated activity against human herpesviruses.

U.S. Pat. No. 3,767,795 Schleicher et al, assigned to Abbott Laboratories, describes a method of preventing or treating herpesvirus infections in animals by administering phosphonoacetic acid or its salts.

U.S. Pat. No. 4,215,113 Eriksson et al, assigned to Astra Lakemedel AB, describes a method of treating virus infections, including herpesvirus, by administering phosphonoformic acid or its salts to infected animals.

U.S. Pat. No. 4,347,360 Ogilvie, discloses compounds such as 9-[[2-hydroxy-1-(hydroxymethyl)-ethoxy]-methyl] adenine and analogues thereof as active against herpes simplex virus.

U.S. Pat. No. 4,355,032 Verheyden et al and U.S. patent application Ser. No. 301,790 Ogilvie both teach that 9-[[2-hydroxy-1-(hydroxymethyl)-ethoxy]methyl] guanine (also known as 9-(1,3-dihydroxy-2-propoxymethyl)-guanine) is active against herpes simplex virus.

Patent Co-operation Treaty Application US82/00/182 K. O. Smith and ens BIO LOGICALS inc., describes synergistic mixtures of 9-[[2-hydroxy-1-(hydroxymethyl)ethoxy]methyl] guanine and PFA or PAA or salts thereof, for use in treatment of herpes virus infected cells.

SUMMARY OF THE INVENTION

In one aspect, the present invention provides the novel guanine derivative, active against herpes simplex virus type I which has the formula:

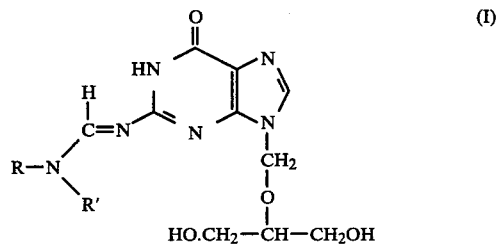

wherein R and R' are independently selected from lower alkyl $C_1$–$C_4$ radicals, namely 2-(N,N-dialkylaminomethylene)-9-[[2-hydroxy-1-(hydroxymethyl)ethoxy]methyl]guanine. Especially preferred is the compound as above in which both R and R' represent methyl, hereinafter sometimes referred to, for brevity, as dimethylaminomethylene-G*.

In another aspect, the present invention provides pharmaceutical compositions for antiviral use, especially anti-herpes use, comprising compounds of formula I as defined above and a suitable pharmaceutically acceptable carrier.

According to another feature of the present invention, there are provided combinations of dimethylaminomethylene-G* with at least one additional pharmaceutically active compound selected from phosphonoformic acid and its salts, phosphonoacetic acid and its salts, various types of interferons (especially interferon α, interferon α and combinations thereof), exhibit synergy as regards their activity towards herpes simplex viruses, especially type 1 viruses, and are extremely active compositions in respect thereof.

A further aspect of the present invention comprises a method of treating viral infections which includes administering to virally infected viable mammalian cells dimethylaminomethylene-G* or compositions thereof with pharmaceutically acceptable carriers or optionally with at least one additional said pharmaceutically active compound.

It will of course be understood that the invention includes the pharmaceutically acceptable salts of dimethylaminomethylene-G*, along with the base compound.

DESCRIPTION OF THE PREFERRED EMBODIMENTS

The compound dimethylaminomethylene-G* can be prepared by a process of nucleophilic addition of the compound 9-[2-hydroxy-1-(hydroxymethyl)ethoxy]methyl]guanine sometimes hereinafter referred to, for brevity, as G* at the 2-amino terminus to form the desired amide, by a process chosen and conducted so that it does not affect other groups on the molecule.

The compound G* of formula:

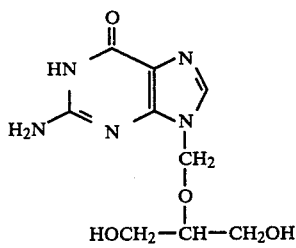

is known, having been disclosed in the aforementioned U.S. patent application Ser. No. 301,790 Ogilvie and related foreign application (e.g. European patent application No. 81304227.2).

Thus the present invention provides a process for preparing 2-(N,N-dialkylaminomethylene)-9-[[2-hydroxy-1-(hydroxymethyl)ethoxy]methyl]guanine of formula I given above which comprises treating G* with the corresponding N,N-dialkylformamidedialkylacetal.

As noted, it has additionally been found that combinations of dimethylaminomethylene-G* and interferon and other known anti-herpes drugs are synergistically active towards herpes simplex type I viral infections. This HSV strain produces virus particles which are partially resistant to one or more drugs used in its treatment. If, however, another drug can be located which has a different mode of action from the first drug, and which will supress the activity of this partially resistant strain, the result may be a synergistic combination of drugs with overall activity against the virus far greater than could be predicted from a consideration of the individual drugs themselves.

Preferred among the drugs for making synergistic combination with dimethylaminomethylene are interferon α, interferon α and mixtures thereof.

The relative amounts of the drugs in the synergistic combinations according to the invention can be varied over wide limits. The optimum amount of each drug varies according to the selection of the drug, the nature of the formulation in which it is to be applied and the severity and location of the infection among other factors.

The invention is further described and illustrated in the following specific non-limiting examples.

EXAMPLE 1

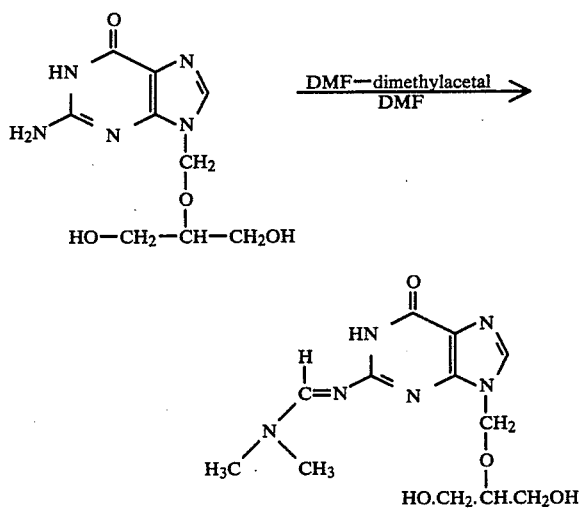

Into a stoppered dry round bottom flask (25 ml capacity) was placed 200 mg of compound II and 5 ml of dry DMF. After stirring for a few minutes at room temperature, 1.5 ml of N,N-dimethylformamidedimethylacetal was added. The mixture was stirred for 14 hours at room temperature during which time the flask was tightly stoppered to avoid moisture contact. Thin layer chromatography (methanol:methylene chloride, 1:2) showed two major spots and showed that the starting material had disappeared completely after addition of reagents.

The mixture was then treated with 10 ml methanol and stirred for 30 minutes at room temperature. The solvents were then evaporated to give 0.522 g of crude product with a characteristic single spot on thin layer chromatography.

The crude solid was crystallized from Methanol, methylene chloride and hexanes at room temperature. A total of 230 mg of colourless crystals were recovered, a 94.6% yield. Melting point 228°–229° C.; UV (0.66 mg in 25 ml MeOH 302;235 nm; NMR (35 mg in DMSO-$d_6$+12 drops $CD_3OD$); δ3.05 (S,3H,N-Me); δ3.15(S,3H,N-Me).

EXAMPLE 2

Dimethylaminomethylene-G* was subjected to testing in vitro, to determine its activity against herpes simplex virus type 1.

Human fetal fibroblasts (HFF) derived from fetal tissues were used in these experiments. Cells were grown and maintained in Basal Medium Eagle (BME) supplemented with 0.112% sodium bicarbonate, 2 mML-glutamine, 2 mg% Neomycin and 20% (vol/vol) calf serum.

HSV-1-Patton strains, well-known, old established strains of herpes simplex virus type 1 were used in the experiments as set out in the tables presented below.

A viral plaque titration method (Roizman and Roane, 1961) was used to determine the titer of the respective HSV type 1. Tissue culture dishes (35 by 10 mm, Corning) were seeded with cells and used for assays when they were approximately 75% monolayer. Volumes (0.2 ml) of logarithmic dilutions of the virus strain were inoculated onto each of two tissue culture dishes and adsorbed for 1 hr with intermittent shaking, the inoculum was removed and 2 ml of 20% BME containing 0.5% human immune serum globulin was added. After a 48 hr. incubation period at 36° C. in a 5% $CO_2$ atmosphere, the overlay medium was removed, and the cell sheets were stained with a 0.05% aqueous crystal violet solution. The plaque numbers were counted with the aid of a Nikon profile projector which magnified the dishes 10×. Duplicate results were averaged, and the number of plaque-forming units (PFU) was calculated. The virus titre is thus expressed as a number of plaque forming units to be seen after growth under these conditons. In order to assess the activity of dimethylaminomethylene-G*, experiments were conducted by plaque titration to determine its viral ED-50 (i.e. the concentration thereof which inhibits HSV plaque formation by 50% in the HFF cells, as compared with cell cultures in the absence of the drug). For this purpose, tissue culture dishes (35 by 10 mm) with HFF cell monolayers at 75% confluence were inoculated with approximately 50 plaque-forming units of virus per 0.2 ml, and the virus was allowed to adsorb for 1 hr with intermittent shaking. After removal of the inoculum, 2 ml of 20% BME with 0.5% immune globulin and various amounts of dimethylaminomethylene-G* in solution were added to duplicate dishes. One set of dishes received no dimethylaminomethylene-G* and was later used for the control. After a 48 hr incubation period at 36° C. in a 5% $CO_2$ atmosphere, the overlay medium was removed, the cells were stained as described above, and plaques were counted. The counts of duplicate plates were averaged.

The results are shown in Table 1 below:

TABLE 1

| Concentration of dimethylaminomethylene-G* (micrograms per ml) | Plaque forming units per dish, HSV-I infected cells |
| --- | --- |
| 0.032 | 47 |
| 0.1 | 46 |
| 0.32 | 47 |
| 1.0 | 36 |
| 3.2 | 13 |
| 10.0 | 0 |

Plotting the above figures on semi-logarithmic graph paper, as numbers of plaque forming units against concentration of drug, allows one to determine the $ED_{50}$ to be 2.7 in respect of HSV-I-Patton strain.

EXAMPLE 3

Following the procedures described above, combinations of dimethylaminomethylene-G* and interferons were tested for anti-viral activity, in vitro.

The viral plaque titration method was used as previously described, with HSV-1-Patton in HFF cells. The interferon used was a mixture of equal portions of human interferon-α and human interferon-α.

The amounts of each drug and virus titer, expressed in plaque-forming units per dish, are given in Table II below. The lower the figure for virus titer, the greater the inhibiting, anti-viral effect of the tested drug or drug combination.

Plotting a graph similar to that discussed in example 2 permits determination of the $ED_{50}$ for the dimethylaminomethylene-G*/interferon combination. By comparing this figure to the $ED_{50}$ for dimethylaminomethylene-G* alone, it becomes evident that a 10 fold reduction in the $ED_{50}$ is achieved, thereby illustrating a synergistic combination of compounds.

TABLE II

| Concentration of dimethylaminomethylene-G* (g/ml) | Concentration of interferon (units/ml) | Titer PFU dish |
| --- | --- | --- |
| 0.032 | 320,320 | 40 |
| 0.1 | 320,320 | 33 |
| 0.32 | 320,320 | 0 |
| 1.0 | 320,320 | 0 |
| 3.2 | 320,320 | 0 |
| 10.0 | 320,320 | 0 |
| 0 | 320,320 | 32 |
| 0 | 0 | 44 |

For administration to patients, the compounds or compositions of the invention may be applied topically as ointment, cream or powder, parenterally, interthecally, as nose drops, eye drops or as an aerosol for inhalation, again depending upon the nature and location of the infection to be treated. Suitable dosage rates are in accordance with those known and established as effective with the other drugs for this purpose. Effective unit doses for administration of the compositions interthecally or parenterally are suitably in the range from about 0.1–100 mg of drug, per kg mammal body weight, most suitably in the 0.5–20 mg per kg and most preferably about 5 mg per kg, on the basis of a dosage administered from 2–4 times daily. It is preferred to treat the infection with relatively large doses of the drug at the outset, so as to limit the chances of development of resistant viral strains in the infection.

For topical administration, ointments or creams in conventional inert bases (e.g. petrolatum, etc.) can be formulated, in the known way. An amount from about 0.1–5 weight percent of drug, preferably from about 0.5–2 weight percent of drug, provides a suitable concentration in an ointment or cream, for topical administration 1–4 times per day. Such topically applied formulations are effectively holding a reservoir of the active drug against the infected site, so that the concentrations of drug in the formulations are not critical, provided of course that a dosage level harmful to surrounding skin areas is not used.

In respect of combinations of drugs according to the present invention, the suitable modes of administration thereof and dosage levels are essentially as discussed above, with the above dosage figures pertaining to the dimethylaminomethylene-G* component of the combination and being normally somewhat lower than those given above.

I claim:

1. The compound 2-(N,N-dialkylaminomethylene)-9-[[2-hydroxy-1-(hydroxymethyl)ethoxy]methyl]guanine of the formula:

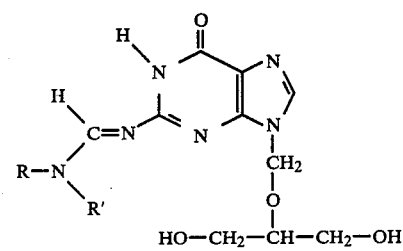

and its pharmaceutically acceptable salts wherein R and R' each represent an independently selected lower alkyl group of 1-4 carbon atoms.

2. The compound of claim 1 wherein R and R' are methyl.

3. A pharmaceutical composition active in combatting herpes virus type 1 infections and consisting essentially of an effective amount of the compound of formula I as given in claim 1 or a pharmaceutically acceptable salt thereof, in admixture with a pharmaceutically acceptable carrier.

4. The compound 2-(N,N-dialkylaminomethylene)-9-[[2-[hydroxy-1-(hydroxymethyl)ethoxy]methyl]guanine.

5. A pharmaceutical composition active in combatting herpes simplex virus type 1 infections and consisting essentially of a first drug which is 2-(N,N-dialkylaminomethylene)-9-[[2-hydroxy-1-(hydroxy methyl)ethoxy]methyl]guanine of the formula given in claim 1 or a pharmaceutically acceptable salt thereof, and a second drug which is selected from the group consisting of interferon, phosphonoformic acid and its salts, and phosphonoacetic acid and its salts.

6. The composition of claim 5 wherein said first drug is 2-(N,N-dimethylaminomethylene)-9-[[2-hydroxy-1-(hydroxymethyl)ethoxy]methyl]guanine.

7. The composition of claim 6 wherein the second drug is interferon, interferon α or a mixture thereof.

8. The composition of claim 6 wherein the second drug is phosphonoformic acid or a salt thereof.

9. The composition of claim 15 wherein the second drug is phosphonoacetic acid or a salt thereof.

10. A method of treating viral infections which comprises administering to virally infected viable mammalian cells an effective amount of 2-(N,N-dialkylaminomethylene)-9-[[2-hydroxy-1-(hydroxymethyl)ethoxy]methyl]guanine or a pharmaceutically acceptable salt thereof, wherein each alkyl group is independently selected from lower alkyl groups of 1-4 carbon atoms.

* * * * *

UNITED STATES PATENT AND TRADEMARK OFFICE
CERTIFICATE OF CORRECTION

PATENT NO. : 4,461,757
DATED : July 24, 1984
INVENTOR(S) : KELVIN K. OGILVIE

It is certified that error appears in the above-identified patent and that said Letters Patent is hereby corrected as shown below:

Column 2, line 54, delete "interferon $\alpha$" (second occurrence) and insert --interferon $\tau$--.

Column 3, line 57, delete "interferon $\alpha$" and insert --interferon $\tau$--.

Column 5, line 58, delete "human interferon $\alpha$" and insert --human interferon $\tau$--.

Column 6, Table II, in the heading insert --($\alpha$, $\tau$)-- under "(units/ml)".

Column 8, claim 7, line 2, after "interferon" (first occurrence) insert --$\tau$--.

Column 8, claim 9, line 1, delete "claim 15" and insert --claim 6--.

Signed and Sealed this

Second Day of April 1985

[SEAL]

Attest:

DONALD J. QUIGG

Attesting Officer

Acting Commissioner of Patents and Trademarks